(12) United States Patent
Lo et al.

(10) Patent No.: US 11,471,110 B2
(45) Date of Patent: Oct. 18, 2022

(54) SMART PAD AND SYSTEM THEREOF

(71) Applicant: Foreaider Co., Ltd., Taichung (TW)

(72) Inventors: I-Lin Lo, Taichung (TW); Yun-Lung Lo, Taoyuan (TW); Pei-Ju Wang, Taichung (TW)

(73) Assignee: Foreaider Co., Ltd.

( * ) Notice: Subject to any disclaimer, the term of this patent is extended or adjusted under 35 U.S.C. 154(b) by 17 days.

(21) Appl. No.: 16/191,560

(22) Filed: Nov. 15, 2018

(65) Prior Publication Data
US 2019/0142348 A1    May 16, 2019

Related U.S. Application Data

(60) Provisional application No. 62/586,928, filed on Nov. 16, 2017.

(51) Int. Cl.
*G06F 3/041*    (2006.01)
*A61B 5/1455*   (2006.01)
(Continued)

(52) U.S. Cl.
CPC ............ *A61B 5/7275* (2013.01); *A61B 5/024* (2013.01); *A61B 5/0205* (2013.01);
(Continued)

(58) Field of Classification Search
CPC ... A61B 5/7275; A61B 5/0816; A61B 5/6892; A61B 5/0205; A61B 5/14552;
(Continued)

(56) References Cited

U.S. PATENT DOCUMENTS 3,653,083 A * 4/1972 Lapidus ............... A47C 27/081
5/713
3,727,606 A * 4/1973 Sielaff .................. A61B 5/113
600/535

(Continued)

FOREIGN PATENT DOCUMENTS

EP     3095704 A1 * 11/2016 ............. B64D 13/08

OTHER PUBLICATIONS

JP2010175050A Pressure Pipe Having Flexibility Nagayoshi Akio; Nagayoshi Seiji (Year: 2010).*

*Primary Examiner* — Gary Jackson
*Assistant Examiner* — Alexander M Eisenberg

(57) ABSTRACT

The invention provides a smart pad for detecting a physiological state and movement, together or individually, of a user. The smart pad comprises: a sensing portion, having a plurality of sub-sensing portions, wherein the plurality of sub-sensing portions are respectively separated from each other by a plurality of partitions; a channel portion, communicating with one opening of each of the plurality of sub-sensing portions; and a collection portion, communicating with the plurality of sub-sensing portions through the channel region. The physiological state and movement, together or individually, is determined according to a fluid status change in the plurality of sub-sensing portions delivered to the collection portion through the channel portion. The interior of the plurality of partitions is separated from the interiors of the sensing portion, channel region, and collection portion.

20 Claims, 7 Drawing Sheets

(51) Int. Cl.
  *A61B 5/08* (2006.01)
  *A61B 5/00* (2006.01)
  *A61B 5/0205* (2006.01)
  *A61B 5/024* (2006.01)

(52) U.S. Cl.
  CPC ........ *A61B 5/0816* (2013.01); *A61B 5/14552* (2013.01); *A61B 5/4812* (2013.01); *A61B 5/6892* (2013.01); *G06F 3/041* (2013.01)

(58) Field of Classification Search
  CPC ......... A61B 5/4812; A61B 5/024; A61B 5/11; A61B 5/1126; G06F 3/041
  USPC ........................................................ 600/300
  See application file for complete search history.

(56) References Cited

U.S. PATENT DOCUMENTS

| | | | | |
|---|---|---|---|---|
| 4,803,744 A | * | 2/1989 | Peck | ............... A61B 5/1115 5/713 |
| 5,853,005 A | * | 12/1998 | Scanlon | ............. A61B 5/113 600/459 |
| 2010/0174199 A1 | * | 7/2010 | Young | ............... A61B 5/411 600/484 |
| 2012/0193211 A1 | * | 8/2012 | Ciesla | ............. G06F 3/0202 200/81 H |
| 2015/0182418 A1 | * | 7/2015 | Zaiss | ............... A61H 1/005 601/57 |

\* cited by examiner

SMART PAD AND SYSTEM THEREOF

CROSS REFERENCE

The present invention claims priority to U.S. Provisional Application No. 62/586,928, filed on Nov. 16, 2017.

BACKGROUND OF THE INVENTION

Field of Invention

The present invention relates to a smart pad, in particular, a smart pad for sensing and detecting a physiological state and movement, together or individually, of a user according to a state change of a fluid in the smart pad.

Description of Related Art

In general, prior physiological state sensing methods, such as, infrared sensing of heartbeat or breathing rates by elastic belts, have a common feature where it must be bound to a user's skin. Usually, direct contact is required for sensing purposes. However, such restraint often causes inconvenience to the user. Some emotionally nervous users may pull out sensors due to discomfort, and even tear the sensors apart during sleep. These types of situations can cause sensing problems. Some conditions, such as breathing suspension, need to be observed continuously during sleep. If a sensor is torn off during sleep, the opportunity for effective first aid during sleep may be lost.

Therefore, sensing technology for physiological states and movements, together or individually, of a user without disturbing the user is very important.

SUMMARY OF THE INVENTION

In view of the above, the present invention provides a smart pad which has the advantages of simple design, easy operation, high monitoring accuracy, and not needing to disturb a user.

In one perspective, the present invention provides a smart pad for detecting a physiological state and movement, together or individually, of a user. The smart pad includes: a sensing portion, including a plurality of sub-sensing portions, which are separated from each other by a plurality of partitions; a channel region, communicating with the plurality of sub-sensing portions; and a collection portion, communicating with a fluid in the plurality of sub-sensing portions through the channel region, wherein a state change of the fluid generated in the plurality of sub-sensing portions corresponding to the physiological state and movement, together or individually, is transmitted to the collection portion through the channel region; wherein, the plurality of partitions is separated from the sensing portion, channel region, and collection portion.

In one embodiment, the plurality of partitions does not accommodate the fluid. In one embodiment, other fluid in the plurality of partitions do not communicate with the fluid in the sensing portion, the channel region, and the collection portion.

In one embodiment, the plurality of partitions does not accommodate the fluid, and the plurality of partitions includes a plurality of partition slots separating the plurality of sub-sensing portions from each other.

In one embodiment, the fluid includes a liquid or a gas.

In one embodiment, the state change of the fluid generated in the sensing portion corresponding to the physiological state and movement, together or individually, is a pressure change or a flow change of the fluid in the sensing portion.

In one embodiment, the state change of the fluid generated in the plurality of sub-sensing portions corresponding to the physiological state and movement, together or individually, is the pressure change of the fluid in the plurality of sub-sensing portions. A transmission direction of a pressure wave in the channel region, and a transmission direction of a pressure wave in the plurality of sub-sensing portions, have an inclination angle therebetween.

In one embodiment, the state change of the fluid generated in the sub-sensing portion corresponding to the physiological state and movement, together or individually, is a pressure change of the fluid in the plurality of sub-sensing portions. The channel region includes a pressure adjusting portion to adjust a distribution of pressure waves (or wave fronts) in the channel region.

In one embodiment, a channel section area of each sub-sensing portion, is smaller than a channel section area of the channel region.

In one embodiment, a channel section area of the channel region along a direction from a plurality of communication portions of the plurality of sub-sensing portions to the collection portion, gradually increases. In another embodiment, a channel section area of the channel region along a direction from the communication portions of the plurality of sub-sensing portions to the collection portion, remains unchanged.

In one embodiment, the physiological state includes: heartbeats, breathing, organ sounds, or sudden deaths. The movement includes: rotations, swinging, pulsations, shaking, muscle fibrillations, contractions, or falling.

In one perspective, the present invention provides a smart pad system for determining a physiological state and movement, together or individually, of a user. The smart pad system includes: a fluid sensing unit, comprising a sensing portion, a channel region, and a collection portion. The channel region communicates with the sensing portion and the collection portion, for transmitting a state change of a fluid in the sensing portion corresponding to the physiological state and movement, together or individually, to the collection portion; a tube, including at least one tube wall, for communicating with the fluid in the collection portion; and a processing unit, determining the physiological state and movement, together or individually, according to the state change of the fluid communicating with the collection portion.

The objectives, technical details, features, and effects of the present invention will be better understood with regard to the detailed description of the embodiments below, with reference to the drawings.

DESCRIPTION OF THE PREFERRED EMBODIMENTS

The drawings as referred to throughout the description of the present invention are for illustrative purpose only, to show the interrelations between the components, but not drawn according to actual scale.

Figure 1:
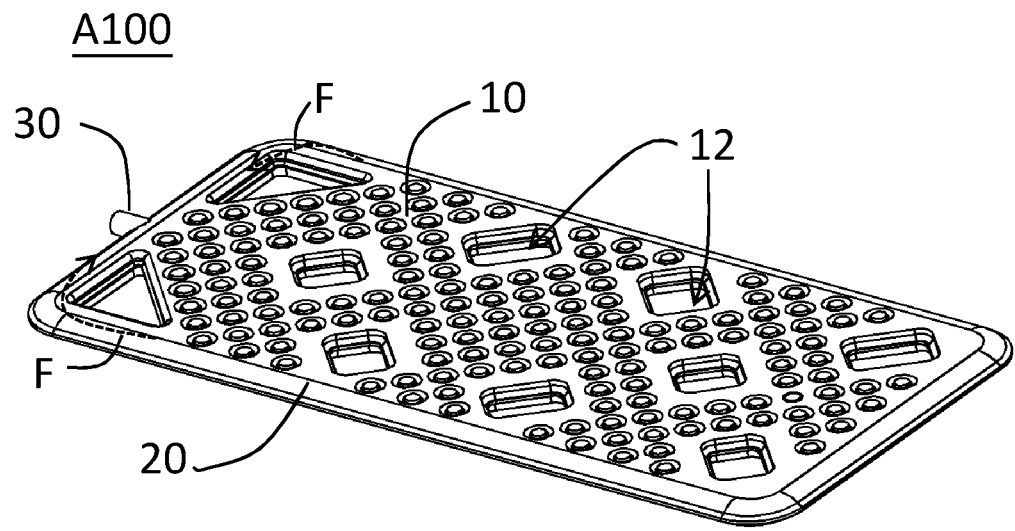
FIGS. 1-5D show a plurality of smart pads respectively according to multiple embodiments of the present invention.
Figure 2:
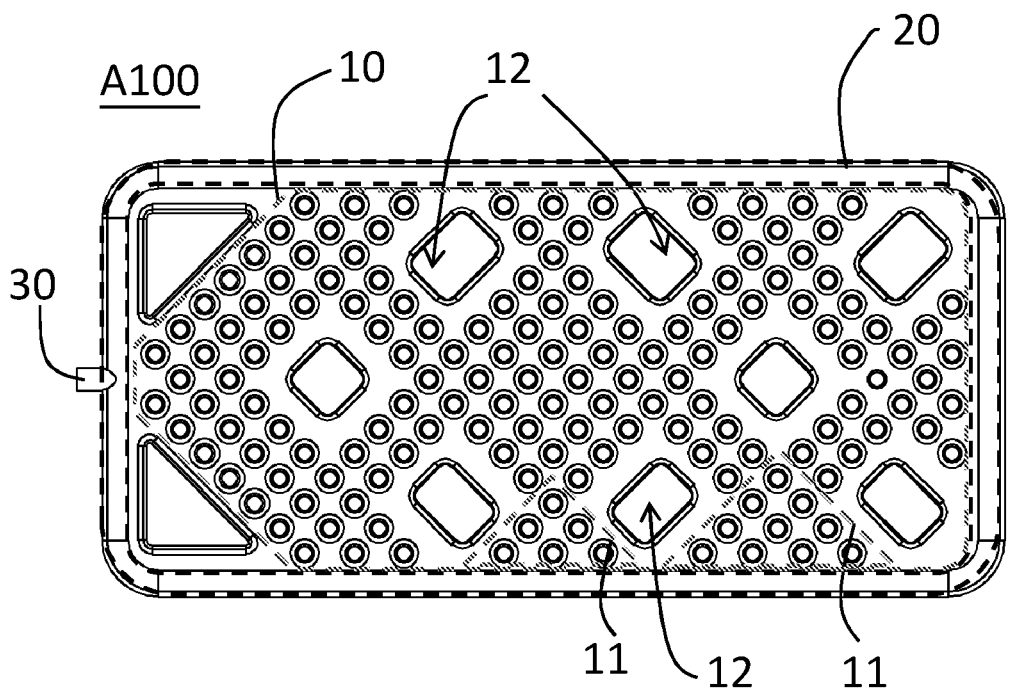

FIGS. 1 and 2 respectively show a 3D view and a top view of a smart pad A100 according to one embodiment of the present invention. The smart pad A100 can be used to determine a physiological state and movement, together or individually, of a user. The smart pad A100 includes: a sensing portion 10, including a plurality of sub-sensing portions 11, wherein the plurality of sub-sensing portions 11 are separated from each other by a plurality of partitions 12; a channel region 20, communicating with the plurality of sub-sensing portions 11; and a collection portion 30, collecting a fluid F in the plurality of sub-sensing portions 11 and/or, for example, through the channel region 20. FIG. 1 shows an outside appearance of the smart pad A100, which includes the internal fluid F (shown by hidden lines, which represent that the fluid F is filled in the smart pad A100). The fluid F corresponds to the physiological state and movement, together or individually, changing states. The state change is transmitted through the channel region 20, to the collection portion 30. The plurality of partitions 12 do not include the fluid F, such that changing states of the fluid F are not generated in the plurality of partitions 12, corresponding to the physiological state and movement, together or individually. Regarding the state change of the fluid F corresponding to the physiological state and movement, together or individually, please refer to the description of the following embodiments.

Figure 3:
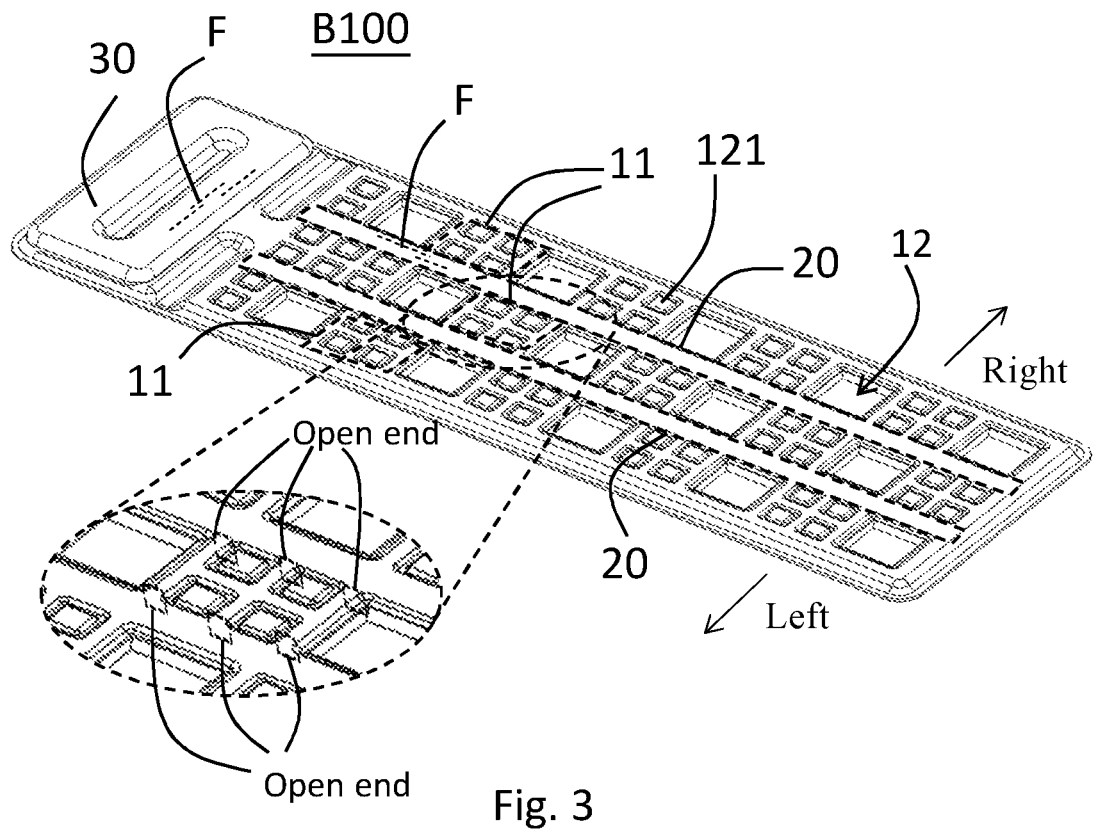

FIG. 3 shows a smart pad B100 according to another embodiment of the present invention. The channel region 20 communicates with two open ends of the plurality of sub-sensing portions 11 (the hidden line show two open ends), or the channel region 20 communicates with two open ends of a portion of the plurality of sub-sensing portions 11 (both open ends of plurality of sub-sensing portions 11, wherein the channel region 20, communicates with the left and right open ends of the plurality of sub-sensing portions 11). The channel region 20 is designed to transmit the state change of the fluid F in the plurality of sub-sensing portions 11 corresponding to the physiological state and movement, together or individually, to the collection portion 30, for determining the physiological state and movement, together or individually, generated in the plurality of sub-sensing portions 11.

Figure 4:
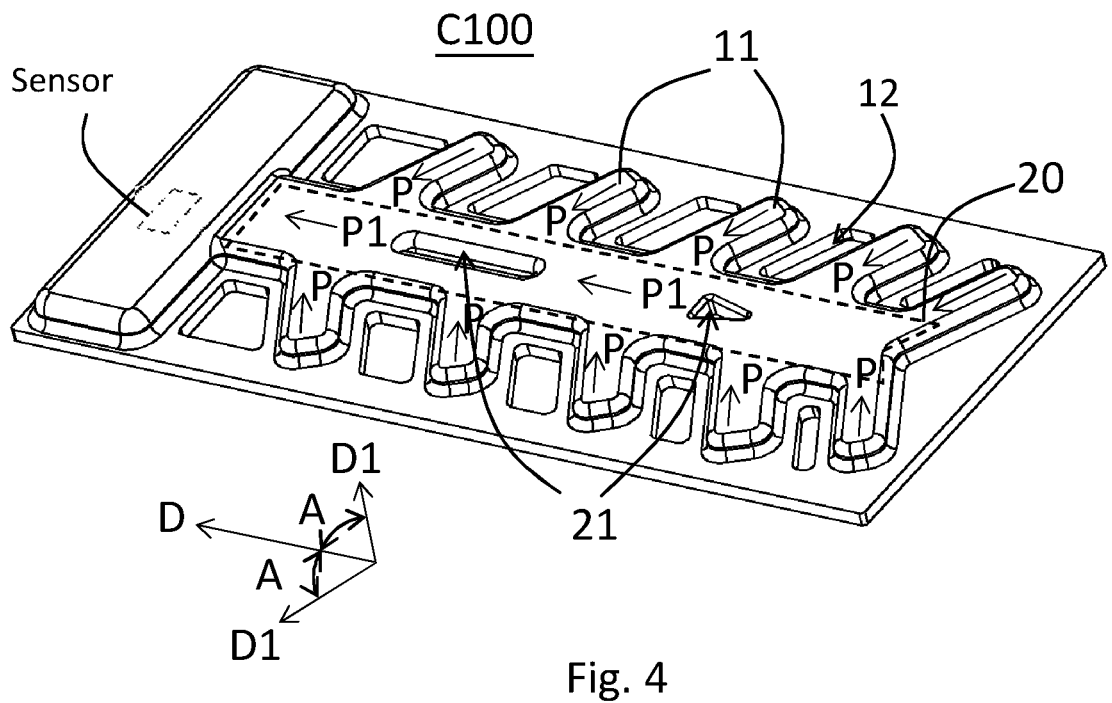

FIG. 4 shows a smart pad C100 according to another embodiment of the present invention. The pressure wave P in the plurality of sub-sensing portions 11, and the pressure wave P1 in the channel region 20, have their own transmission directions D and D1. According to FIG. 4, the transmission direction D and the transmission direction D1, have an inclination angle A therebetween. The inclination angle A is preferably less than 90 degrees, in order to avoid mutual interference between the pressure waves P and P1. The inclination angle A is used to guide the pressure waves P and P1, forward to the channel region 20. In one embodiment, the pressure waves P and P1 can represent a wave front of the pressure waves from the plurality of sub-sensing portions 11 and the channel region 20.

Figure 5A:
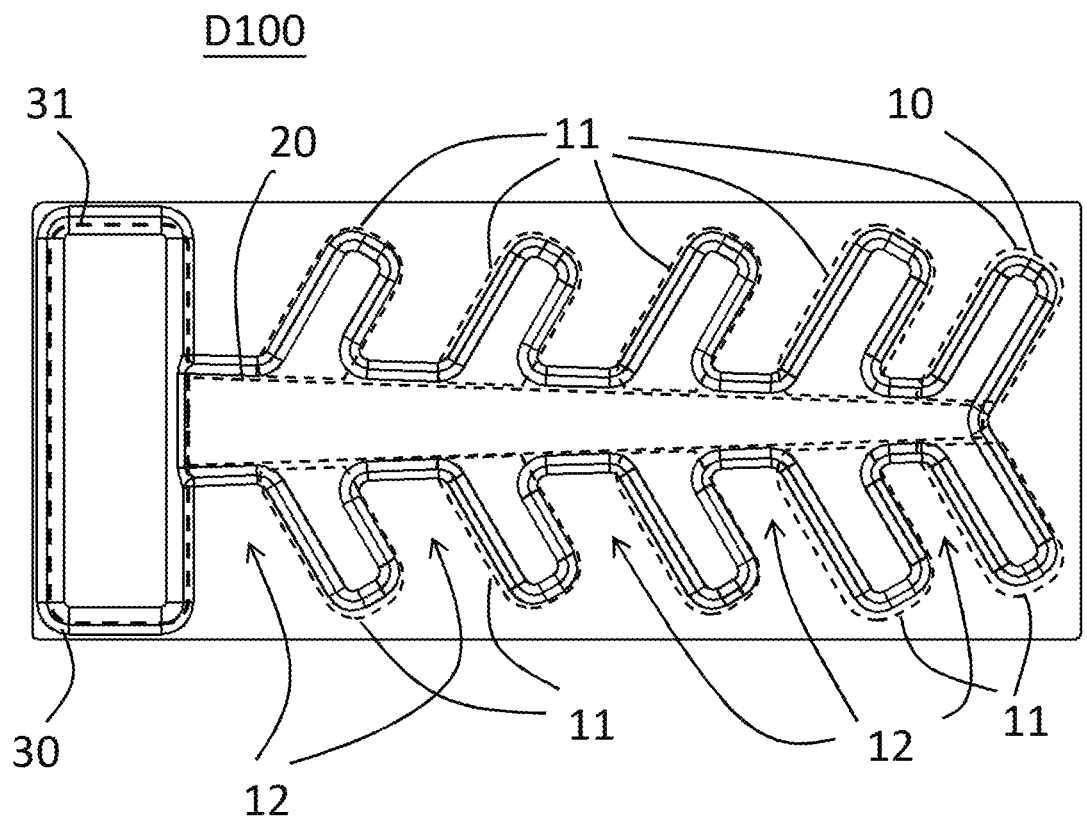

FIG. 5A shows a smart pad D100 according to another embodiment of the present invention. The smart pad D100 includes: a sensing portion 10, including a plurality of sub-sensing portions 11, wherein the plurality of sub-sensing portions 11 are separated from each other by a plurality of partitions 12 (the plurality of sub-sensing portions 11 of the smart pad D100 in FIG. 5A, and the plurality of sub-sensing portions 11 of the smart pad A100 in FIG. 2, are separated from each other by the plurality of partitions 12, wherein the difference between FIGS. 2 and 5A is the plurality of sub-sensing portions 11 of the smart pad D100 do not communicate with each other, but at least a portion of the plurality of sub-sensing portions 11 of the smart pad A100 communicate with each other); a channel region 20, communicating with the plurality of sub-sensing portions 11; and a collection section 30, wherein the fluid F in the plurality of sub-sensing portions 11, communicates with the collection section 30 through the channel region 20 (the collection portion 30 of the smart pad D100 in FIG. 5A, includes a buffering portion 31, and the collection portion 30 of the smart pad A100 in FIG. 2, does not include a buffering portion. The design of the buffering portion depends on practical needs). The buffering portion is located in the collection portion 30, which has a bag-like structure for accommodating the fluid F. However, according to the present invention, the buffer portion is not limited to the collection portion 30, but can be disposed at other positions of the smart pad to communicate with the channel region 20. Similarly, the smart pad D100 of FIG. 5A has the fluid F inside (shown by hidden lines, which mean that it is filled inside the smart pad D100). The fluid F is filled in the plurality of sub-sensing portions 11, and a state change of the fluid F can be generated corresponding to the physiological state and movement, together or individually. The state change is transmitted through the channel region 20, to the collection portion 30. The plurality of partitions 12 do not include the fluid F, such that changing states of the fluid F are not generated in the plurality of partitions 12, corresponding to the physiological state and movement, together or individually. Regarding the state change of the fluid F generated corresponding to the physiological state and movement, together or individually, please refer to the description of the following embodiments.

The smart pad provided by the present invention has the advantages of simple design, easy operation, and not needing to disturb a user. In particular, the user can sit, or lie, on the smart pad for sensing of a physiological state and movement, together or individually, of the user without any other disturbance to the user.

In one embodiment, the physiological state of the user can include heartbeats, pulses, respiration, organ sounds, blood pressure, or blood oxygen saturation levels. In general, the frequency of a heartbeat is about 1 Hz, and the frequency of breathing is about 0.1 Hz. The heartbeat or breathing of a user provides vibrations from a force or position change of the user. The user can directly contact the smart pad by sitting, or lying, or indirectly contact the smart pad D100 via another pad (such as a mattress, or bedding). The force or position change from the user can be transmitted to the fluid F in the smart pad, to drive the fluid F to generate the state change correspondingly; for example, the pressure change or flow change of the fluid F in the plurality of sub-sensing portions 11. According to the present invention, the physiological state and movement, together or individually, is not limited to the heartbeat or breathing, but can be any physiological state and movement, together or individually, corresponding to the state change of the fluid F.

Figure 5B:
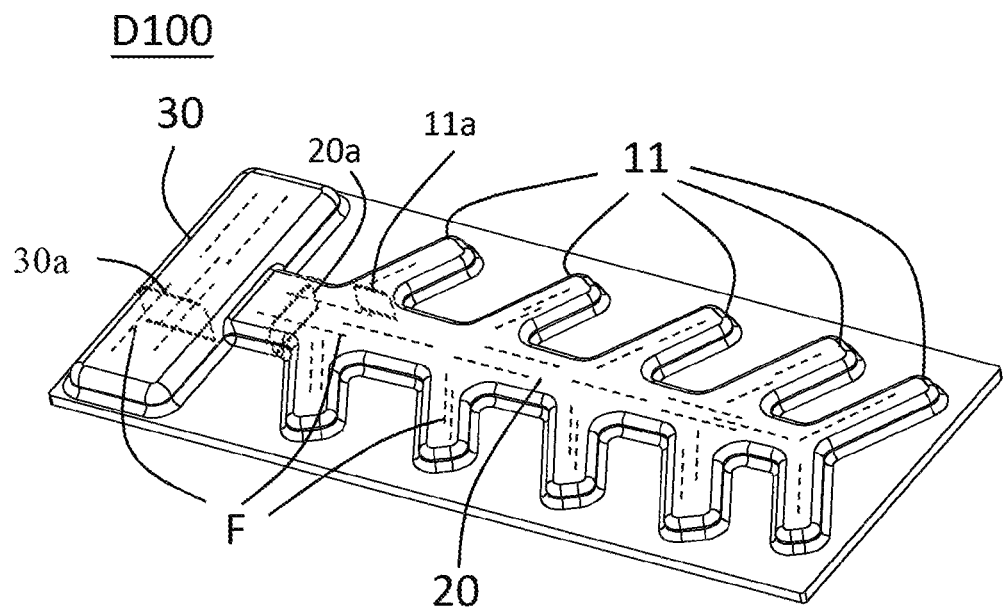
Figure 5C:
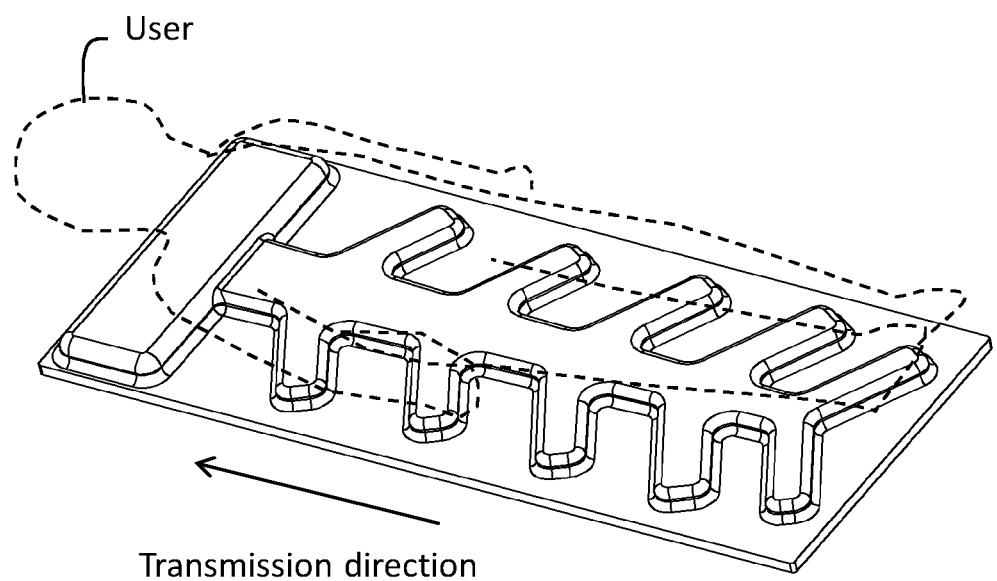
Figure 5D:
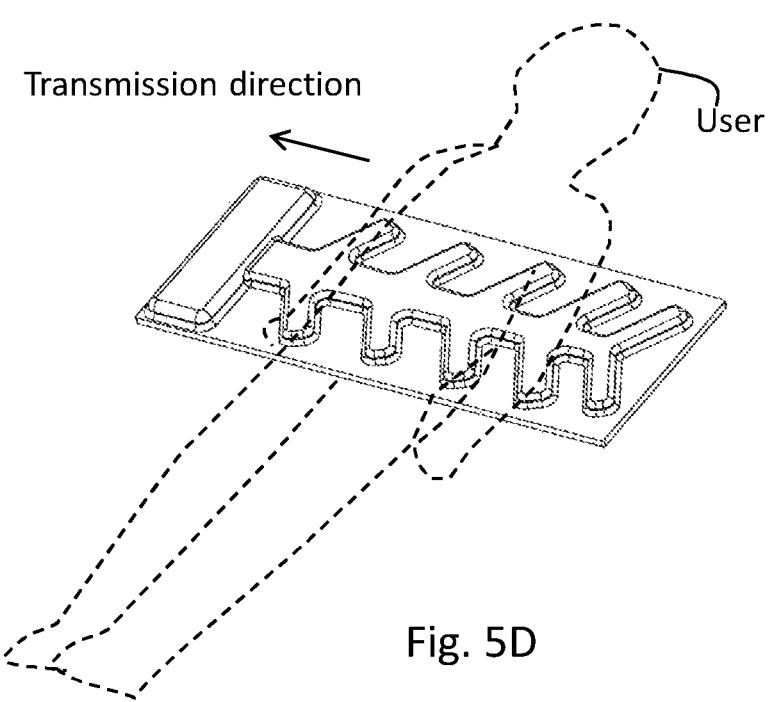

In one embodiment, when using the smart pad, t-ea user can lie thereon in alignment with a transmission direction of the fluid F flowing to the collection portion 30 (FIG. 5C). Or, the user can lie thereon not in alignment with the transmission direction of the fluid F flowing to the collection portion 30 (for example, perpendicular to the transmission direction, FIG. 5D). In the perpendicular example to the transmission direction, different sensing results can be obtained according to different state changes of the fluid F generated in different locations in the smart pad. For example, the movements of the user can be determined, by different sensing results respectively corresponding to the different state changes of the fluid F in different locations in the smart pad. Therefore, a movement such as turning over can be determined by the smart pad of the present invention. For one example shown in FIG. 5D, a user's position on the smart pad can be decided based on the user's main sensing position, so that a higher sensitive sensing result can be obtained.

In particular, the physiological state of the user determined according to the present invention, can also include breathing suspension, which can be determined according to the signal characteristics in the time domain or the frequency domain. When breathing suspension is determined, a warning signal can be sent in time to remind of a first aid emergency, to avoid missing an effective time period for first aid.

When a user is a pregnant woman, the smart pad can be used to sense the pregnant woman and an intra-abdominal fetus, to perform sensing of heartbeats or breathings of the pregnant woman and the intra-abdominal fetus. The sensing function is available for the intra-abdominal fetus, having a heart function which is not fully developed, yet still may be sensed. Further, after birth, when the baby is suffocating due to poor breathing, or under a physiological state such as sudden death, sensing can occur in time for promptly reminding of a first aid emergency.

In addition to a user's movement, such as contact, no contact, contact with applying gravity, or moving of the user with contact on the smart pad, in one embodiment, the movement can include: rotations, swinging, pulsations, shaking, muscle fibrillations, contractions, molars, or a sleeping status. These movements can be sensed by the smart pad provided by the present invention. For example, when a user is directly or indirectly lying on the smart pad for a long time, decubitus is easily caused due to maintaining of a fixed posture. Decubitus is usually caused by long-term compression of the skin of a user and a bed. For caring purposes, these long-term compressions must be changed by moving the patient regularly for easing symptoms. However, long-term compression locations are hidden between a user and a bed, which is not easy to find by sight. It is necessary to check often to avoid symptoms, causing a caring burden. By the invention, the user's movement is sensed, and when the user does not move for a long time, a warning message is issued to remind a caregiver, to check the patient, and move the user.

In one embodiment, the channel region 20 in FIG. 5B communicates with the plurality of sub-sensing portions 11, at one open end of the plurality of sub-sensing portions 11 (in FIG. 5B, the hidden line shows the open end). However, in the smart pad B100, the channel region 20 communicates with two open ends of the plurality of sub-sensing portions 11, or the channel region 20 communicates with two open ends of a portion of plurality of sub-sensing portions 11. The channel region 20 is designed to transmit the state change of the fluid F in the plurality of sub-sensing portions 11 corresponding to the physiological state and movement, together or individually, to the collection portion 30, for determining the physiological state and movement, together or individually, generated in the plurality of sub-sensing portions 11. The channel region 20 of the smart pad A100 of FIG. 2 similarly communicates with the plurality of sub-sensing portions 11 as in the smart pads D100 and B100, and for details reference can be made to the descriptions of FIGS. 5B and 3.

In one embodiment, referring to FIG. 3, the plurality of partitions 12 do not include the fluid F, and can include a plurality of partition slots or partition pads between the plurality of sub-sensing portions 11, or a combination of the two. The aforementioned partition pads 121 can increase the receiving area of the force or position change generated according to the physiological state and movement, together or individually, of the user, transmitting to the partition pads 121, to increase the sensing sensitivity of the smart pad B100.

In one embodiment, the partition 12 can include another fluid (not shown), and the other fluid does not communicate with the sensing region 10, the channel region 20, and the collection portion 30. In one embodiment, the other fluid has an independent function; for example, regulating a temperature of the smart pad. The other fluid can be individually designed, such as gas and liquid. In one embodiment, the plurality of partitions 12 do not include the other fluid, but are partition slots between the plurality of sub-sensing portions 11. For example, in FIGS. 1, 3, and 4, the plurality of partitions 12 are partition slots between the plurality of sub-sensing portions 11.

The fluid of the aforementioned embodiment can include a liquid or a gas. For example, the gas can include an inert or non-inert gas, and the fluid can be determined according to fluid mechanics characteristics used in the smart pad.

In one embodiment, the state change of the fluid F in the plurality of sub-sensing portions 11 corresponding to the physiological state and movement, together or individually, is the pressure change of the fluid F in the plurality of sub-sensing portions 11. For example, the state change of the fluid generated in the plurality of sub-sensing portions 11 corresponding to the physiological state and movement, together or individually, can be a pressure wave P according to a heartbeat rate or breathing. The pressure wave P in the plurality of sub-sensing portions 11, communicates with the collection portion 30, through the channel region 20 (refer to FIGS. 5B and 3).

Referring to the smart pad A100 in FIGS. 1 and 2, the channel region 20 is located on both sides of the smart pad A100, wherein the transmission directions of the pressure waves in the plurality of sub-sensing portions 11 and the channel region is not limited by the aforementioned angle range of less than 90 degrees.

In one embodiment, the state change of the fluid F generated in the plurality of sub-sensing portions 11 corresponding to the physiological state and movement, together or individually, is the pressure change of the fluid F in the plurality of sub-sensing portions 11. The plurality of partitions 12 of the present invention have a function of reducing a direct impact from the pressure wave to the collection portion 30, to avoid inaccurate sensing results of the sensor caused by the direct impact. The aforementioned buffering portion 31 also has the effect of reducing the direct impact from the pressure wave P to the collection portion 30. In one embodiment, if the buffering portion 31 causes a insufficient pressure in the collection portion 30 for sensing purposes, the smart pad may not include the buffering portion 31.

The sensing method according to the present invention is not limited to the pressure wave, but can be a flow change of the fluid F in the plurality of sub-sensing portions 11. For example, in the smart pad B100 in FIG. 3, a user's heartbeat or breathing vibration generates a force or position change on the smart pad, which is transmitted to the fluid F in each sub-sensing portion 11, to drive the fluid F in the plurality of sub-sensing portions 11 to generate a flow state change corresponding to the heartbeat or breathing vibration. When the flow rate of the fluid F in the plurality of sub-sensing portions 11 is changed, the flow rate communicates with the channel region 20, and the collection portion 30 (in this embodiment, the collection portion 30 has the buffering portion 31). The fluid F in the sensing portion 10, the channel region 20, and the buffering portion 31 is a closed internal fluid. When the fluid F in the plurality of sub-sensing portions 11 is squeezed, and the fluid F flows to the channel region 20. The fluid F in the channel region 20 is squeezed into the buffering portion 31, so that the fluid F flow in the buffering portion 31 increases. Or, when the squeezing is reduced, the fluid F in the buffering portion 31 reflows into the plurality of sub-sensing portions 11 through the channel region 20. Therefore, the flow of the fluid F in the plurality of sub-sensing portions 11 can be sensed.

When sensing the fluid F flow in the buffering portion 31, the plurality of sub-sensing portions 11 also have the pressure wave therein, wherein the transmission directions of the pressure waves from the plurality of sub-sensing portions 11 are parallel to each other in the channel region 20, having limited influence on fluid flow sensing. Therefore, the inclination angle A does not need to be less than 90 degrees, and a designer can determine the angle according to needs.

In one embodiment, the state change of the fluid F generated in the plurality of sub-sensing portions 11 corresponding to the physiological state and movement, together or individually, is the pressure change of the fluid F generated in the plurality of sub-sensing portions 11. Referring to FIG. 4, in the smart pad C100, the channel region 20 includes a pressure adjusting portion 21 to adjust the distribution of pressure waves P1 (or, wave front) in the channel region 20. The design of the pressure adjusting portion 21 is to adjust the pressure waves P1 in the channel region 20 to synchronously move forward, parallel in the transmission direction D1, without interfering with each other. The pressure adjusting portion 21 can be designed as a slot structure in the channel region 20 or other structure having a pressure regulating function. The pressure adjusting portions 21 is not limited by the amounts, positions or shapes shown in the figures. The amounts, e-positions or shapes of the pressure adjusting portions 21 can be determined according to needs. The design of the pressure adjusting portion is a selective design. In one embodiment, the channel region design can have no pressure adjusting portions (FIGS. 1 and 2), to transmit the state change of the fluid F generated in the plurality of sub-sensing portions 11.

In one embodiment, a cross-sectional area of the channel section 11a of each sub-sensing portion 11 (refer to the cross-sectional area of the opening of the plurality of sub-sensing portions 11 in FIG. 5B), is smaller than a cross-sectional area of the channel section 20a of the channel region 20. In one embodiment, the cross-sectional area of the channel section 20a is smaller than a cross-sectional area of the section 30a of the buffer portion 31 of the collection portion 30. The cross-sectional area of the channel section 11a of each sub-sensing portion 11 can be the same as needed, or can have a plurality of different cross-sectional areas. The cross-sectional area of the channel section 11a of each sub-sensing portion 11 can be an average cross-sectional area 11a of all plurality of sub-sensing portions 11, or an equivalent cross-sectional area based on the fluid mechanics characteristics. Further, the cross-sectional area of the channel section 20a of the channel region 20, and the cross-sectional area of the section 30a of the buffering portion 31 can be an average cross-sectional area or equivalent cross-sectional area based on the fluid mechanics characteristics.

In one embodiment, the cross-sectional area of the channel section of the channel region 20 along a direction passing a plurality of communication portions of the plurality of sub-sensing portions 11 to the collection portion 30, gradually increases (for example, the cross-sectional area in the transmission direction D in FIG. 4). In another embodiment, the cross-sectional area of the channel section of the channel region along the direction passing the communication portions of the plurality of sub-sensing portions to the collection portion, remains unchanged (FIG. 3).

The geometry of the opening or section of the aforementioned embodiment is not limited to the pattern in the figures, and it can be determined as needed.

In one embodiment, a material of the sensing portion, the channel region, and the collection portion is preferred to be a polymer material, such as a rubber or a plastic material, wherein the polymer material has a hardness of 68~74 PHR (parts per hundreds of rubber/resin).

According to the present invention, the physiological state and movement, together or individually, of the user can be directly determined according to the state change of the fluid F in the collection portion 30. For example, a sensor (FIG. 4) is placed in the collection portion 30, and the sensing result is transmitted to outside for further processing. However, the implementation of the present invention is not limited thereto, and the physiological state and movement, together or individually, of the user can be sensed and determined outside of the collection portion 30.

Figure 6:
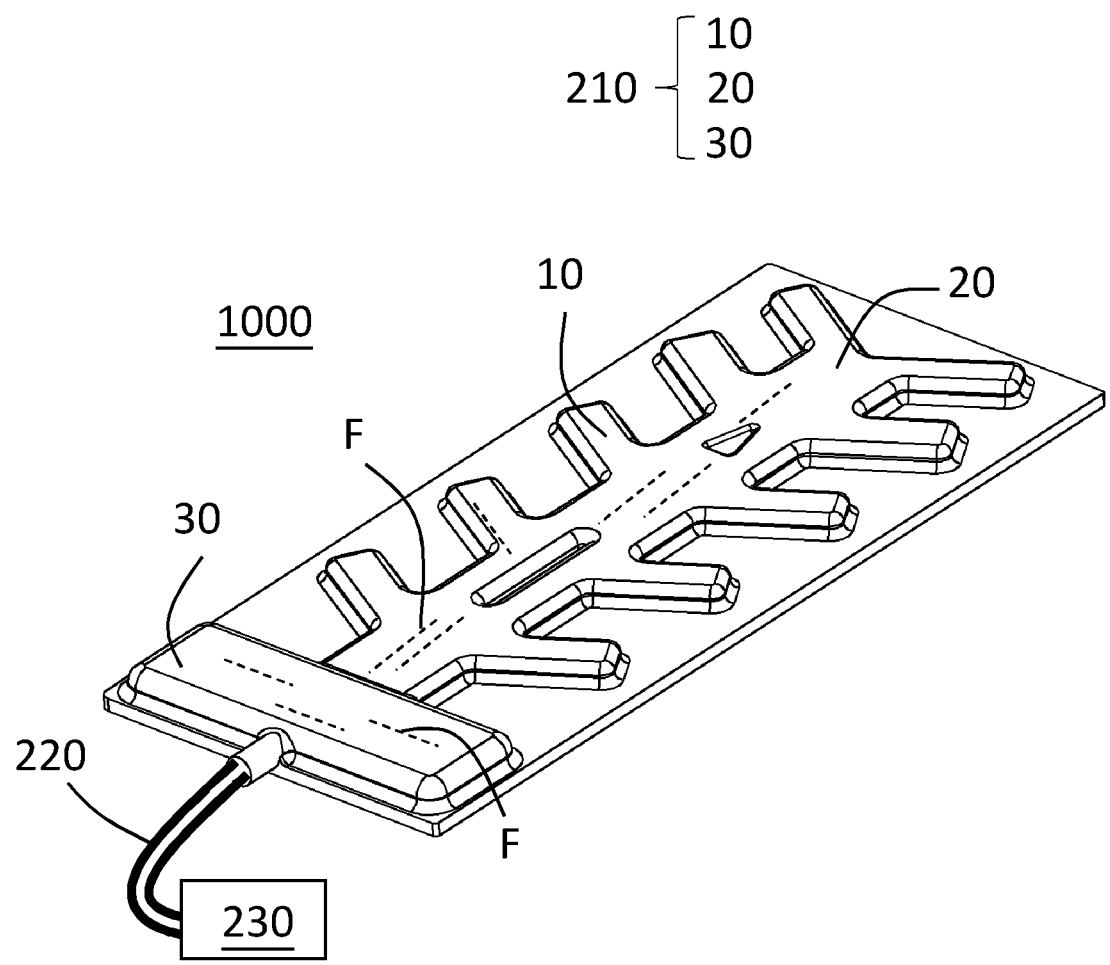
FIG. 6 shows a smart pad system according to one embodiment of the present invention.

In one perspective, the present invention provides a smart pad system for determining a physiological state and movement, together or individually, of a user. According to FIG. 6, the smart pad system 1000 includes: a fluid sensing unit 210, including a sensing portion 10, a channel region 20, and a collecting portion 30. The channel region 20 communicates with the sensing region 10 and the collection portion 30, and the channel region 20 transmits the state change of the fluid F generated in the sensing region 10 corresponding to the physiological state and movement, together or individually, to the collection portion 30; a tube 220, including at least one tube wall 221, communicates with the fluid F in the collection portion 30; a processing unit 230, communicating with the collection portion 30 through the tube 220 to determine the state change of the fluid F, and to determine the physiological state and movement, together or individually, according to the state change of the fluid F. Regarding detailed description of the sensing portion 10, the channel region 20, and the collection portion 30, please refer to the details of the aforementioned embodiment.

Figure 7A:
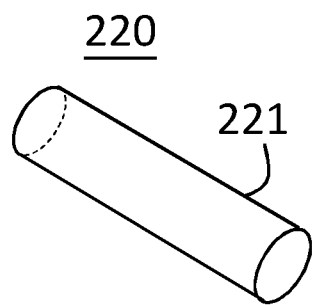
FIGS. 7A and 7B show two tubes respectively according to two embodiments of the present invention.
Figure 7B:
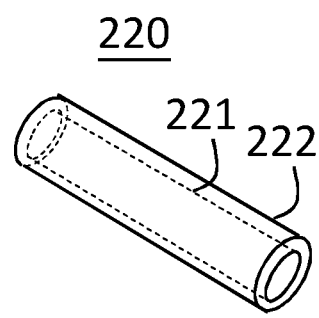

The above-mentioned tube 220, can transmit the state change of the fluid F in the collection portion 30, to the processing unit 230 for determining the physiological state and movement, together or individually, wherein the tube 220 has at least one tube wall 221. FIG. 7A shows a section of the tube 220. The tube 220 includes a tube wall 221, and the tube wall 221 has a closed interior. The tube wall 221 can enclose the fluid F from outside interference which may affect the fluid state change. Please refer to FIG. 7B, in another embodiment, the tube 220 has at least two tube walls: an inner tube wall 221 enclosing the fluid F, and an outer tube wall 222 isolating the fluid F and the inner tube wall 221 from outside interference which may affect the fluid state change. The inner tube wall 221 and the outer tube wall 222 can be combined by close adhesion, or separated from each other. In one embodiment, the inner tube wall 221 is made by a softer material with respect to the outer tube wall 222, to reduce the outside effect on the fluid state change. In one embodiment, a material between the inner tube wall 221 and the outer tube wall 222 can include air, or porous materials (such as sponges, and foams), or be filled with noise-reducing materials.

The aforementioned processing unit 230, can be used for different sensing purposes, such as for a pressure sensor or a flow sensor. The pressure sensor can determine the state change of the fluid F in the tube 221. The flow sensor can determine the flow change of the fluid F in the tube 221, which is transmitted from the sensing portion 10. In this way, the processing unit 230 can determine the physiological state and movement, together or individually, of the user.

In one embodiment, the sensor can include an O-ring to increase the sealing effect of the fluid F in the smart pad system, and also to increase the pressure or flow sensing effect.

Further, the smart pad of the present invention can also include a microphone (or pressure sensor) (not shown, the disposed position can be determined according to needs) to assist determination of snoring or breathing suspension. Further, the smart pad can also include an infrared sensor (not shown, the disposed position can be determined according to needs) to continuously sense a temperature of a special part of a user to improve determination accuracy of decubitus.

In one embodiment, the smart pad can also determine the state change of the fluid according to a physiological state and movement, together or individually, for sensing falling, when trying to get up, or sudden deaths, reminding a caregiver to perform first aid.

Figure 8:
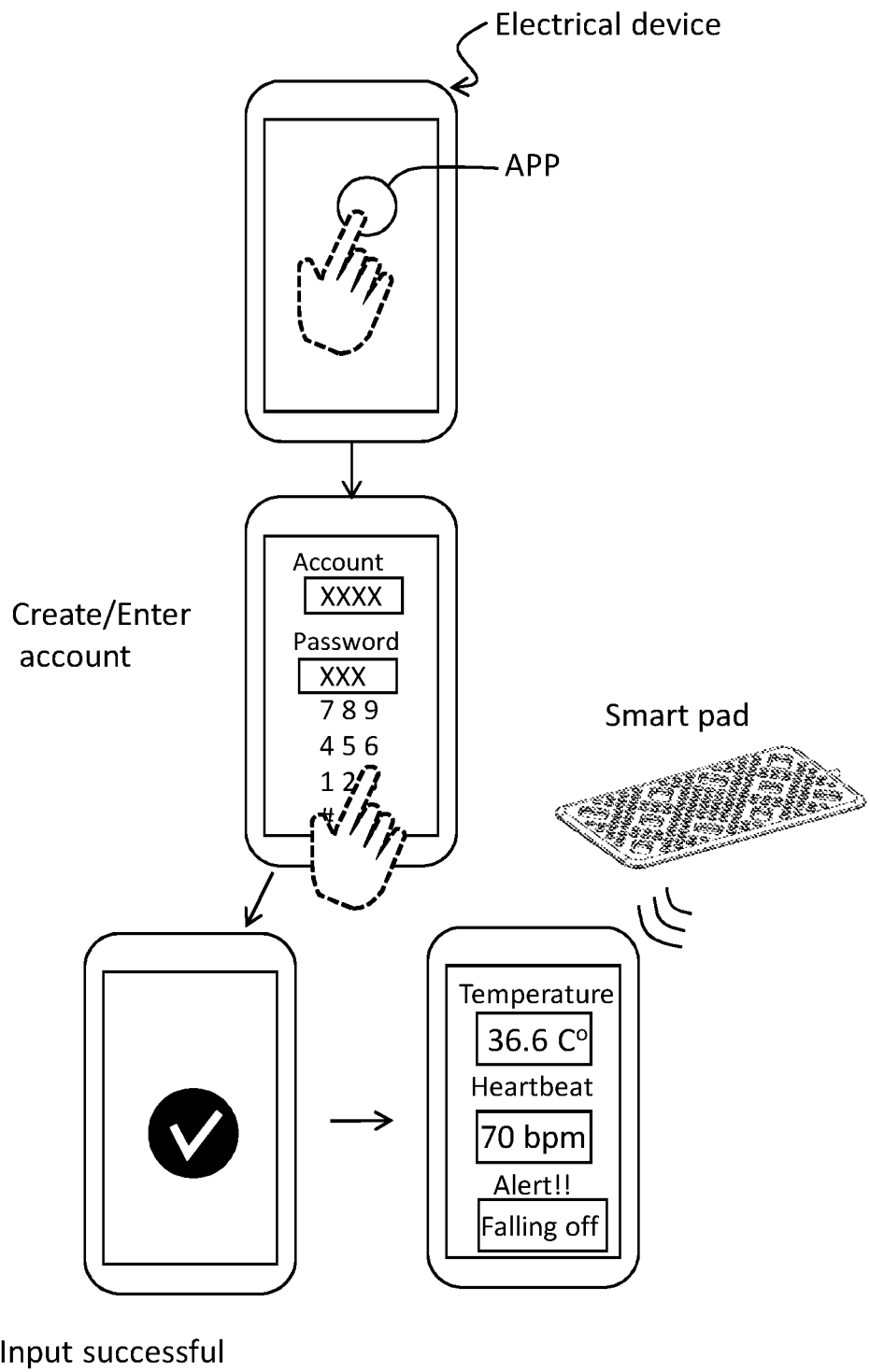
FIG. 8 shows an operation of an APP interface according to one embodiment of the present invention.

In one embodiment of the present invention, another user such as a caregiver, can obtain the physiological state and movement, together or individually, of a user by an APP input interface on an electrical device. The APP input interface can receive the physiological state and movement, together or individually, of the user through the internet, a telecom network, an IoT network (for example, through an IoT protocol such as WIFI, Wi-SUN, Modbus, Zigbee, IQRF, Thread, ZWAVE, BACnet, LonWorks, M-bus, DALI, EnOcean, RS485, RS232, or KNX), or any wire/wireless signal transmission connected to the smart pad. Please refer to FIG. 8, in one example, the caregiver can enter the APP by clicking on an APP icon, and enter the APP interface to create an account. When the APP interface is connected to the smart pad for obtaining information and the account is successful, several physiological states/movements of the user are shown in the user interface of the electrical device. The caregiver can directly obtain the information without disturbing the user. If an alert occurs, the caregiver can perform first aid as soon as possible. Importantly, the caregiver can obtain the user's state information without often visiting the user's bed. The APP is connected to the smart pad.

The present invention has been described in considerable detail with reference to certain preferred embodiments thereof. It should be understood that the description is for illustrative purpose, not for limiting the scope of the present invention. Those skilled in this art can readily conceive variations and modifications within the spirit of the present invention. Besides, an embodiment or a claim of the present invention does not need to attain or include all the objectives, advantages or features described in the above. The abstract and the title are provided for assisting searches and not to be read as limitations to the scope of the present invention. It is not limited for each of the embodiments described hereinbefore to be used alone; under the spirit of the present invention, two or more of the embodiments described hereinbefore can be used in combination. For example, two or more of the embodiments can be used together, or, a part of one embodiment can be used to replace a corresponding part of another embodiment. All such modifications and variations should fall in the scope of the present invention.

What is claimed is:

1. A smart pad, configured for sensing a physiological state and movement, together or individually, of a user, comprising:
   a sensing portion, comprising a plurality of sub-sensing portions, which are separated from each other by a plurality of partitions;
   a channel region, communicating directly and individually with each of the plurality of sub-sensing portions; and
   a collection portion, communicating directly with the channel region, configured as a reservoir, collecting fluid from the plurality of sub-sensing portions and through the channel region, wherein a state change of the fluid generated in the plurality of sub-sensing portions, corresponding to the physiological state and movement, together or individually, of the user, is transmitted to and agglomerated within the collection portion through the channel region,
   wherein a shape of the channel region is an elongated quadrilateral prism shape having a first elongated side and a second elongated side, the second elongated side opposite the first elongated side, whereby at least one of each of the plurality of sub-sensing portions communicates directly and individually with the channel region via the first elongated side and at least one of each of the plurality of sub-sensing portions communicates directly and individually with the channel region via the second elongated side, and
   wherein the fluid comprises a liquid or a gas and the state change of the fluid is a pressure change or a flow change of the fluid,
   whereby the sensing portion, channel region and collection portion all form the smart pad, and pressure waves of the pressure changes in each of the plurality of sub-sensing portions communicate directly and individually with the channel region, before travelling through the channel region to communicate directly with the collection portion.

2. The smart pad according to claim 1, wherein the plurality of partitions comprises a plurality of partition slots which separate the plurality of sub-sensing portions from each other.

3. The smart pad according to claim 1, wherein when the state change of the fluid in the sensing portion corresponding to the physiological state and movement, together or individually, is the pressure change of the fluid generated in the plurality of sub-sensing portions, an inclination angle of less than 90° degrees is formed between at least one of the plurality of sub-sensing portions and the channel region, whereby the at least one of the plurality of sub-sensing portions angles away from the collection portion such that a transmission direction of a pressure wave from the at least one of the plurality of sub-sensing portions is guided toward a same direction as a transmission direction of a pressure wave from the channel region to the collection portion.

4. The smart pad according to claim 1, wherein when the state change of the fluid in the sensing portion corresponding to the physiological state and movement, together or individually, is the pressure change of the fluid generated in the plurality of sub-sensing portions, the channel region comprises a pressure adjusting portion to adjust distribution of pressure waves therein, whereby the pressure adjusting portion is a fixed and unmovable slot structure, the fixed and unmovable slot structure completely surrounded by fluid on a circumference thereof in the channel region.

5. The smart pad according to claim 1, wherein a cross-sectional area of a channel section of each of the plurality of sub-sensing portions, formed between the plurality of sub-sensing portions and channel region, is smaller than a cross-sectional area of a channel section of the channel region.

6. The smart pad according to claim 1, further comprising a buffering portion, located in the collection portion, wherein a pressure or flow impact on the collection portion, caused by the state change of the fluid in the channel region corresponding to the physiological state and movement, together or individually, is reduced by the buffering portion.

7. The smart pad according to claim 1, wherein a material of the sensing portion, the channel region, and the collection portion is made of a polymer, rubber or plastic material, having a hardness of 68~74 PHR rubber.

8. The smart pad according to claim 1, wherein the collection portion comprises a sensor, sensing a state change of the fluid generated in the plurality of sub-sensing portions, corresponding to the physiological state and movement, together or individually, of the user.

9. The smart pad system according to claim 1, wherein the elongated quadrilateral prism shape is a trapezoidal prism shape, and the elongated quadrilateral prism shape further comprises a bottom elongated trapezoid shaped base and a top elongated trapezoid shaped base, the top elongated trapezoid shaped base parallel and facing the bottom elongated trapezoid shaped base, the bottom elongated trapezoid shaped base connecting to the top elongated trapezoid shaped base via the first elongated side and the second elongated side, respectively.

10. The smart pad system according to claim 9, wherein the elongated quadrilateral prism shape further comprises an opening side and a closed side, the opening side opposite the closed side, the opening side connecting to the closed side via the first elongated side, the bottom elongated trapezoid shaped base, the second elongated side, and the top elongated trapezoid shaped base, respectively, whereby an area of the opening side is greater than an area of the closed side, and whereby the collection portion is in direct fluid communication with the channel region via the opening side.

11. A smart pad system, configured for sensing a physiological state and movement, together or individually, of a user, comprising:
   a fluid sensing unit, comprising a sensing portion having a plurality of sub-sensing portions, which are separated from each other by a plurality of partitions, a channel region, communicating directly and individually with each of the plurality of sub-sensing portions, and a collection portion, communicating directly with the channel region, configured as a reservoir, collecting fluid from the plurality of sub-sensing portions and through the channel region, wherein the channel region communicates directly and individually with each of the plurality of sub-sensing portions and the collection portion, respectively, for transmitting a state change of a fluid generated in the plurality of sub-sensing portions corresponding to the physiological state and movement, together or individually, of the user, to the collection portion, and wherein the fluid agglomerates within the collection portion through the channel region;
   a tube, comprising at least one tube wall, for communicating with the fluid in the collection portion; and
   a processing unit, determining the physiological state and movement, together or individually, of the user, according to the state change of the fluid communicating with the fluid in the collection portion,
   wherein a shape of the channel region is an elongated quadrilateral prism shape having a first elongated side and a second elongated side, the second elongated side opposite the first elongated side, whereby at least one of each of the plurality of sub-sensing portions communicates directly and individually with the channel region via the first elongated side and at least one of each of the plurality of sub-sensing portions communicates directly and individually with the channel region via the second elongated side, and
   wherein the fluid comprises a liquid or a gas and the state change of the fluid is a pressure change or a flow change of the fluid,
   whereby the sensing portion, channel region and collection portion all form the smart pad, and pressure waves of the pressure changes in each of the plurality of sub-sensing portions communicate directly and individually with the channel region, before travelling through the channel region to communicate directly with the collection portion.

12. The smart pad system according to claim 11, wherein when the state change of the fluid in the sensing portions corresponding to the physiological state and movement, together or individually, is a pressure change of the fluid generated in the plurality of sub-sensing portions, an inclination angle of less than 90° degrees is formed between at least one of the plurality of sub-sensing portions and the channel region, whereby the at least one of the plurality of sub-sensing portions angles away from the collection portion such that a transmission direction of a pressure wave from the at least one of the plurality of sub-sensing portions is guided toward a same direction as a transmission direction of a pressure wave from the channel region to the collection portion.

13. The smart pad system according to claim 11, wherein the at least one tube wall comprises an inner tube wall and an outer tube wall, wherein a material of the inner tube wall is softer than a material of the outer tube wall, and a material between the inner tube wall and the outer tube wall is air, porous material, or noise-reducing material.

14. The smart pad system according to claim 11, wherein the collection portion comprises a sensor, sensing a state change of the fluid generated in the plurality of sub-sensing portions, corresponding to the physiological state and movement, together or individually, of the user, whereby the processing unit is electrically coupled to the sensor.

15. The smart pad system according to claim 11, wherein the plurality of partitions comprises a plurality of partition slots which separate the plurality of sub-sensing portions from each other.

16. The smart pad system according to claim 11, wherein when the state change of the fluid in the sensing portion corresponding to the physiological state and movement, together or individually, is a pressure change of the fluid generated in the plurality of sub-sensing portions, the channel region comprises a pressure adjusting portion to adjust distribution of pressure waves therein, whereby the pressure adjusting portion is a fixed and unmovable slot structure, the fixed and unmovable slot structure completely surrounded by fluid on a circumference thereof in the channel region.

17. The smart pad system according to claim 11, wherein a cross-sectional area of a channel section of each of the plurality of sub-sensing portions, formed between the plurality of sub-sensing portions and channel region, is smaller than a cross-sectional area of a channel section of the channel region.

18. The smart pad system according to claim 11, wherein a material of the sensing portion, the channel region, and the collection portion is made of a polymer, rubber or plastic material, having a hardness of 68~74 PHR rubber.

19. The smart pad system according to claim 11, wherein the elongated quadrilateral prism shape is a trapezoidal prism shape, and the elongated quadrilateral prism shape further comprises a bottom elongated trapezoid shaped base and a top elongated trapezoid shaped base, the top elongated trapezoid shaped base parallel and facing the bottom elongated trapezoid shaped base, the bottom elongated trapezoid shaped base connecting to the top elongated trapezoid shaped base via the first elongated side and the second elongated side, respectively.

20. The smart pad system according to claim 19, wherein the elongated quadrilateral prism shape further comprises an opening side and a closed side, the opening side opposite the closed side, the opening side connecting to the closed side via the first elongated side, the bottom elongated trapezoid shaped base, the second elongated side, and the top elongated trapezoid shaped base, respectively, whereby an area of the opening side is greater than an area of the closed side, and whereby the collection portion is in direct fluid communication with the channel region via the opening side.

* * * * *